United States Patent
Raus et al.

(10) Patent No.: US 9,844,683 B2
(45) Date of Patent: Dec. 19, 2017

(54) DEVICE FOR PERCUTANEOUS INTERSTITIAL BRACHYTHERAPY

(71) Applicant: Laura Raus, Rome (IT)

(72) Inventors: Laura Raus, Rome (IT); Fabrizio Caroli, Rome (IT)

(73) Assignee: Laura Raus, Rome (IT)

( * ) Notice: Subject to any disclaimer, the term of this patent is extended or adjusted under 35 U.S.C. 154(b) by 275 days.

(21) Appl. No.: 14/443,621

(22) PCT Filed: Nov. 28, 2012

(86) PCT No.: PCT/IT2012/000360
§ 371 (c)(1),
(2) Date: May 18, 2015

(87) PCT Pub. No.: WO2014/083584
PCT Pub. Date: Jun. 5, 2014

(65) Prior Publication Data
US 2015/0273237 A1    Oct. 1, 2015

(51) Int. Cl.
*A61N 5/10*    (2006.01)
*A61B 90/00*    (2016.01)

(52) U.S. Cl.
CPC ............ *A61N 5/1007* (2013.01); *A61B 90/39* (2016.02); *A61N 5/1027* (2013.01);
(Continued)

(58) Field of Classification Search
CPC .. A61N 5/1001; A61N 5/1007; A61N 5/1014;
A61N 5/1015; A61N 5/1027; A61N 2005/1008; A61N 2005/1009; A61N 2005/101; A61N 2005/1011; A61M 37/0069
See application file for complete search history.

(56) References Cited

U.S. PATENT DOCUMENTS 6,007,474 A * 12/1999 Rydell ................. A61N 5/1007
                                                              600/7
6,790,210 B1    9/2004 Cragg et al.
(Continued)

OTHER PUBLICATIONS

PCT International Search Report dated Apr. 3, 2013 for International Application No. PCT/IT2012/000360 filed on Nov. 28, 2012 in the name of Laura Raus.
(Continued)

*Primary Examiner* — Charles A Marmor, II
*Assistant Examiner* — Thaddeus Cox
(74) *Attorney, Agent, or Firm* — Steinfl + Bruno LLP (57) ABSTRACT

A portable device for insertion of radioactive seeds in percutaneous interstitial brachytherapy applications is described. The device includes: an elongated main body in form of a handpiece; a shielded container of radioactive seeds, received within the main body and having a rotating drum suitable, in use, to release one or more radioactive seeds from the container; means for driving the rotating drum, activatable by an operator and based on lever mechanisms and gears; and means for introducing one or more radioactive seeds in a body site of interest, comprising a substantially wire-shaped pusher. The pusher urges the radioactive seed(s) released from the rotating drum through a cannula unit.

21 Claims, 4 Drawing Sheets

(52) U.S. Cl.
CPC .... *A61N 5/1048* (2013.01); *A61B 2090/3966* (2016.02); *A61N 5/1015* (2013.01); *A61N 2005/101* (2013.01); *A61N 2005/1009* (2013.01); *A61N 2005/1024* (2013.01); *A61N 2005/1074* (2013.01); *A61N 2005/1094* (2013.01)

(56) References Cited

U.S. PATENT DOCUMENTS

| | | |
|---|---|---|
| 2002/0193656 A1 | 12/2002 | Ravins et al. |
| 2003/0018232 A1 | 1/2003 | Elliott et al. |
| 2003/0109769 A1* | 6/2003 | Lowery ............. A61M 37/0069 600/7 |
| 2010/0234669 A1 | 9/2010 | Armstrong et al. |
| 2013/0178822 A1* | 7/2013 | Hickingbotham . A61B 17/3468 604/506 |
| 2014/0180065 A1* | 6/2014 | Garcia ................... A61B 19/54 600/424 |

OTHER PUBLICATIONS

PCT Written Opinion dated Apr. 3, 2013 for International Application No. PCT/IT2012/000360 filed on Nov. 28, 2012 in the name of Laura Raus.

* cited by examiner

DEVICE FOR PERCUTANEOUS INTERSTITIAL BRACHYTHERAPY

CROSS REFERENCE TO RELATED APPLICATIONS

The present application is the US national stage of International Patent Application No. PCT/IT2012/000360 filed on Nov. 28, 2012.

TECHNICAL FIELD OF THE INVENTION

The present invention refers to a device for interstitial brachytherapy applications, performed percutaneously, particularly suitable for the treatment of primitive and secondary bone tumours, including those from localizations of hemolymphoproliferative diseases, and of malignant tumours of soft tissues.

BACKGROUND

Brachytherapy, also known as "internal radiotherapy", is a treatment based on radiation administration, used above all for arresting tumour cell multiplication.

The treatment is based on the depositing of radioactive sources—typically in the form of one or more so-called "seeds"—directly in tumour tissue or in that surrounding the tumour growth. The implanted radioactive seed releases a radiation dose uninterruptedly, during a short period of time in the case of temporary implants, or for the entire effective life-time, to a decay, in case of permanent implants.

Currently, two typologies of brachytherapic treatment are practiced, i.e.:
   intracavitary treatments, in which the sources are placed in body cavities close to the tumour volume; and
   interstitial treatments, in which the sources are implanted within the tumour volume.

However, generally the brachytherapic treatments currently adopted, and the associated instruments, provide extremely invasive procedures for the depositing in situ of the sources and cannot be applied—or can be in a very limited manner only—to bone tumours, e.g. those of the vertebral column. In particular, some specific body districts, and among these the vertebral bodies, are today hardly accessible or completely inaccessible with available instruments.

Also due to such difficulties, currently the radiotherapy of bone tumours in general, and of those of the vertebral column in particular, is typically performed with radiation therapy administrations from the outside.

Said external radiotherapy, however performed—for instance with a linear accelerator (LINAC), with intensity-modulated radiation therapy (IMRT), that is, collimated beams that reach the tumour, with image-guided radiation therapy (IGRT), or, again, with tomotherapy, which is a form of radiation therapy that uses TC to treat the tumour—has to pass through healthy tissues that, in many cases, are subjected to the same radiation as tumour tissues (in the best of hypotheses at a lower dose in the above-mentioned collimated-beam mode).

Moreover, an external radiation therapy treatment is generally administered in a daily single-dose for a sequence of several weeks to reach the optimum therapeutic dose, in an attempt to minimize damages to healthy tissues and increase the probability that tumour cells be exposed to radiations at a stage in which they appear sensitive to DNA damaging. However, this makes the treatment lengthy, costly and physically stressful for the patient.

US 2010/0234669 discloses a brachytherapy application for the treatment of bone tumours based on a cannula that is inserted in the body district of interest and through which radioactive elements are introduced.

SUMMARY OF THE INVENTION

The technical problem set and solved by the present invention is to provide a device suitable for brachytherapy treatment of bone tumours allowing to overcome the drawbacks mentioned above with reference to the known art.

Such a problem is solved by a device according to claim 1.

Preferred features of the present invention are object of the dependent claims.

The device of the invention is suitable for interstitial brachytherapy applications, by percutaneous route. It is specifically contrived for the treatment of tumours of the vertebral column, and in particular of vertebral bodies; in fact, the overwhelming majority of vertebral secondary lesions are localized in this site.

The present invention provides some relevant advantages.

First of all, the device of the invention allows an effective treatment of primary and secondary neoplastic bone lesions. In particular, the device is specifically suitable for the treatment of spinal metastases and vertebral lesions due to hematological pathologies in the vertebral body, of malignant vertebral tumours and, in general, of bone tumours. The device is also suitable to the treatment of malignant soft-tissue sarcomas.

The device of the invention acts percutaneously, thereby being minimally invasive, by depositing in situ only the radioactive seeds, effective for locoregional treatment, and removing the seed-applying device immediately after the end of the procedure.

The device of the invention allows the depositing of radioactive seeds in a precisely selected dose, according to the specific needs of the patient and the evolution of the treatment.

The device also allows an extremely accurate placing of one or more radioactive seeds in a pre-programmed position, in the anatomic site of interest. In particular, the device of the invention allows the depositing of radioactive seeds, interstitially, within the bone tissue. In case of vertebral applications, seeds can be inserted into a cavity obtained by the surgeon in the vertebral body with methods already known.

Therefore, the invention allows to avoid exposing healthy tissues to radiation, precisely thanks to the possibility of an accurate prearrangement of doses and a precise positioning of the radioactive sources.

Preferably, the insertion procedure is performed through an anatomical route, such as the vertebral peduncles, which being continual with the body represent the most correct approach, all intrabone, for depositing the seeds in intrasomatic tumour lesions.

Preferably, the device is provided with applying cannulas, intentionally of a diameter such as to facilitate the progress of seeds but impede seed deviation from the longitudinal axis, with a jamming and a consequent stacking thereof. The applying cannulas connected to the device handpiece allow in fact to introduce them inside other cannulas, of greater diameter, the latter cannulas stably driven into the vertebral body (through the articular process and the peduncle, beyond the posterior wall of the body of the vertebrae).

According to the preferred embodiments illustrated hereinafter, the weight of the device is greatly reduced.

Other advantages, features and the modes of employ of the present invention will be made apparent in the following detailed description of some embodiments, given by way of example and not for limitative purposes.

BRIEF DESCRIPTION OF THE FIGURES

Reference will be made to the figures of the annexed drawings, wherein.

DETAILED DESCRIPTION OF PREFERRED EMBODIMENTS

Figures 1, 1A:
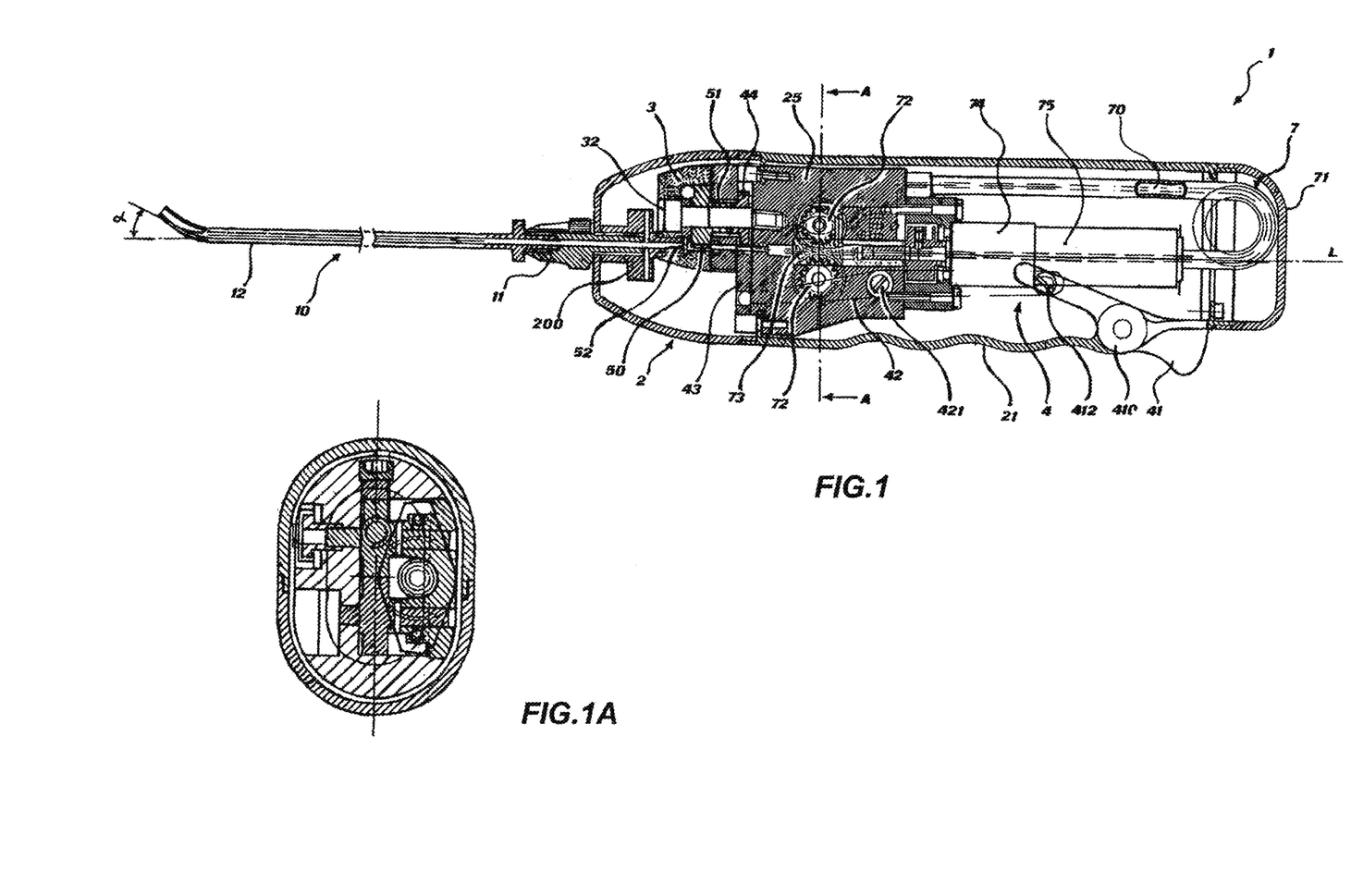
FIG. 1 shows a side sectional view of a device according to a preferred embodiment of the invention.
FIG. 1A shows a sectional view of the device of FIG. 1, taken along line A-A of the latter.

Referring initially to FIGS. 1 and 1A, a device apt to the percutaneous insertion of radioactive seeds in a body site of interest according to a preferred embodiment of the invention is globally denoted by 1.

The device 1 is specifically suitable to the application for brachytherapy treatments of bone tumours, in particular of the vertebral column.

The device 1 comprises a main body 2, or casing, substantially in the form of a handpiece that can be grabbed by an operator. To this end, the main body 2 advantageously bears a handgrip profile 21 obtained, in the present example, at a bottom and proximal portion thereof.

The main body 2 is of substantially elongated shape, and intended to be grabbed, lifted and manipulated by the operator with only one hand. In use, a longitudinal axis L of the device 1 is typically arranged substantially vertical.

The device 1 is portable, in the sense that it can be easily carried according to specific logistical needs of intervention.

Within the main body 2 a container 3 is housed which receives, in use, a plurality of radioactive seeds. The container 3 is shielded, in the sense of constituting a barrier to the outletting of radiations emitted by seeds received therein.

The container 3 comprises a rotating drum 30 which is suitable, in use, to release one radioactive seed at a time from the container 3 itself, to the ends of their insertion in the body site of interest. In the present example, the release of one radioactive seed at a time is provided.

Figure 2:
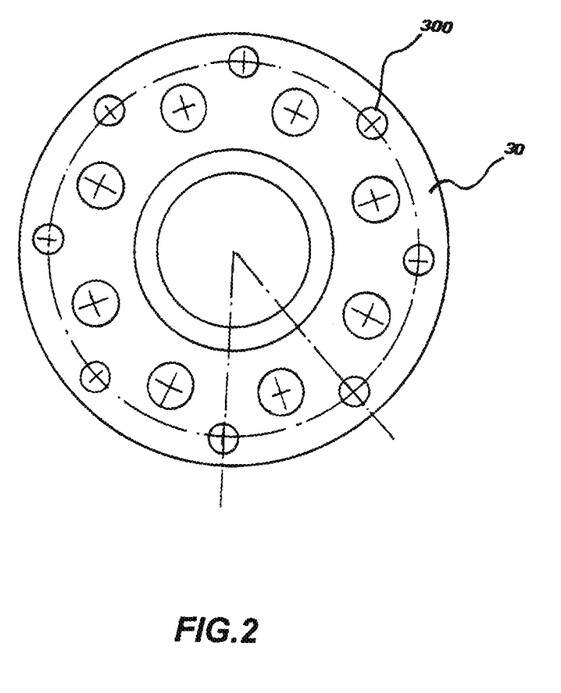
FIG. 2 shows a front view of a rotating drum of the device of FIG. 1.

As shown in greater detail in FIG. 2, the rotating drum 30 is configured as a sort or radial magazine, or carousel, providing just a plurality of radial seats, each one suitable to receive one or more radioactive seeds, one seed in the present example. One of such seats is denoted by 300 in FIG. 2. Always in the present example, the seats 300 are arranged substantially aligned along a single circumference of the magazine and substantially equidistant the one from the other.

As said above and always referring to FIG. 1, the rotating drum 30 can be driven in rotation for ejecting a radioactive seed from the container 3. This is obtained by dedicated driving means, globally denoted by 4 and activatable by an operator.

In the present embodiment, such means 4 for driving the drum 30 mainly comprises a plurality of levers or lever mechanisms, and in particular:

a first lever 41 in the form of a trigger, directly actuatable by the operator; such first lever 41 is configured as a class 1 lever pivotable about a central fulcrum 410 made by a pin;

a second lever 42, pivotally connected, at one end thereof, to one end of the first lever 41, in particular by a pin 412; also the second lever 42 is configured as a class 1 lever, bearing in turn a fulcrum 421 made by a pin.

The second lever 42 is pivotally connected, at one end thereof opposite to that of connection with the first lever 41, with a rack 43.

The overall arrangement is such that the actuation of the trigger, or first lever 41, causes the sliding of the rack 43 in a specially provided stationary guide obtained in the main body 2. In the example depicted in FIG. 1, the overall arrangement is moreover such that the rack 43 is suitable to slide in a substantially vertical direction, upward following an actuation of the trigger 41 and downward when the latter is released.

The rack 43 in turn engages a gear 44 or a suitable conjugated profile, in turn fixed or anyhow associated to the rotating drum 30.

The arrangement is such that the rotation of the drum 30 is one-sense and causes the release of a radioactive seed from the respective seat 300 of the drum 30 itself. To this end, a stepped rotation mechanism is associated to the drum.

The seed thus released comes to be placed within a longitudinal guide path 50 and is ready to be delivered to the outside of the cannula according to modes that will presently be illustrated. The radioactive seed is held from sliding in said path (i.e., horizontally, in the position shown in FIG. 1) by a proximal fall-preventing gasket 51 and by a distal silicone membrane 52 arranged at opposite sides of the path 50 with respect to the position of seed release from the magazine 30. Of course, holding means different from such membrane and gasket may be provided.

Preferably, the container 3 and/or its rotating drum 30 are removably connected to the main body 2, so as to be able to be removed and replaced with a loaded container/drum, or removed, reloaded and then re-inserted in the main body 2 itself. To this end, removable connecting means is provided, in the present example a screw 32 or equivalent elements.

The device 1 moreover comprises means for introducing one or more radioactive seeds in the body site of interest, globally denoted by 7 and suitable to cooperate with a cannula unit 10 that will be described hereinafter. the introducing means 7 comprises a substantially wire-shaped pusher 70, suitable to urge within the site of interest the radioactive seed released from the drum 30 in the guide path 50. In the present embodiment the pusher is flexible, so as to be able to follow a path, even convoluted, within the main body 2. Preferably, the pusher is made of an inert polymer.

The pusher 70 slides within the main body 2 in a pusher-holding element 71.

The latter is a substantially tubular body which defines the path of the pusher 70 within the main body 2, receiving it just thereinside. Exiting the pusher-holding element 71, the pusher 70 is engaged and dragged by gears, in particular by a pair of helical wheels 72. The latter are in turn actuated by an engagement element 73, preferably in the form of an endless screw, of a reducer unit 74 associated to a motor 75, preferably a micromotor. Reducer 74 and motor 75 are both housed within the main body 2 and associated to a bearing 25 thereof. To the reducer 74 or the motor 75 an encoder or an equivalent detection means for controlling the extent of the advancement of the pusher 70 may be associated. Motor 75 and reducer 74 enable a motion in the two directions, to allow both the advancement and the retraction of the pusher 70.

Variant embodiments of the introducing means 7 may provide mechanisms for actuating the pusher 70 different from the hereto-described ones, based or not based on the use of gears.

The introducing means 7 of the pusher 70 and the means 4 for driving the rotating drum 30 are operatively associated therebetween so that the driving of the drum 30 causes also the activation of the motor 75. In particular, it is provided a synchronization such that the distal end of the pusher 70 goes at or in proximity of the seed released from the drum 30 itself.

Figure 3:
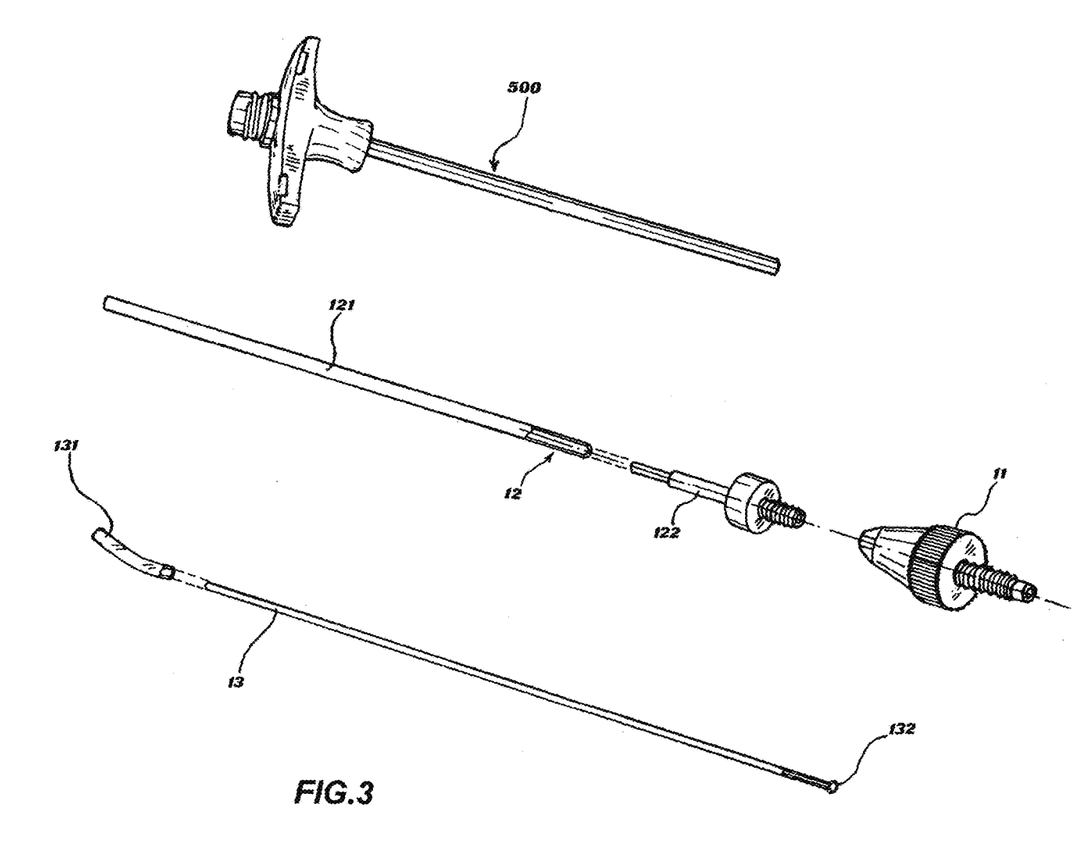
FIG. 3 shows an exploded side view of some components of a cannula unit of the device of FIG. 1, in a disassembled condition.
Figures 4, 5A, 5B:
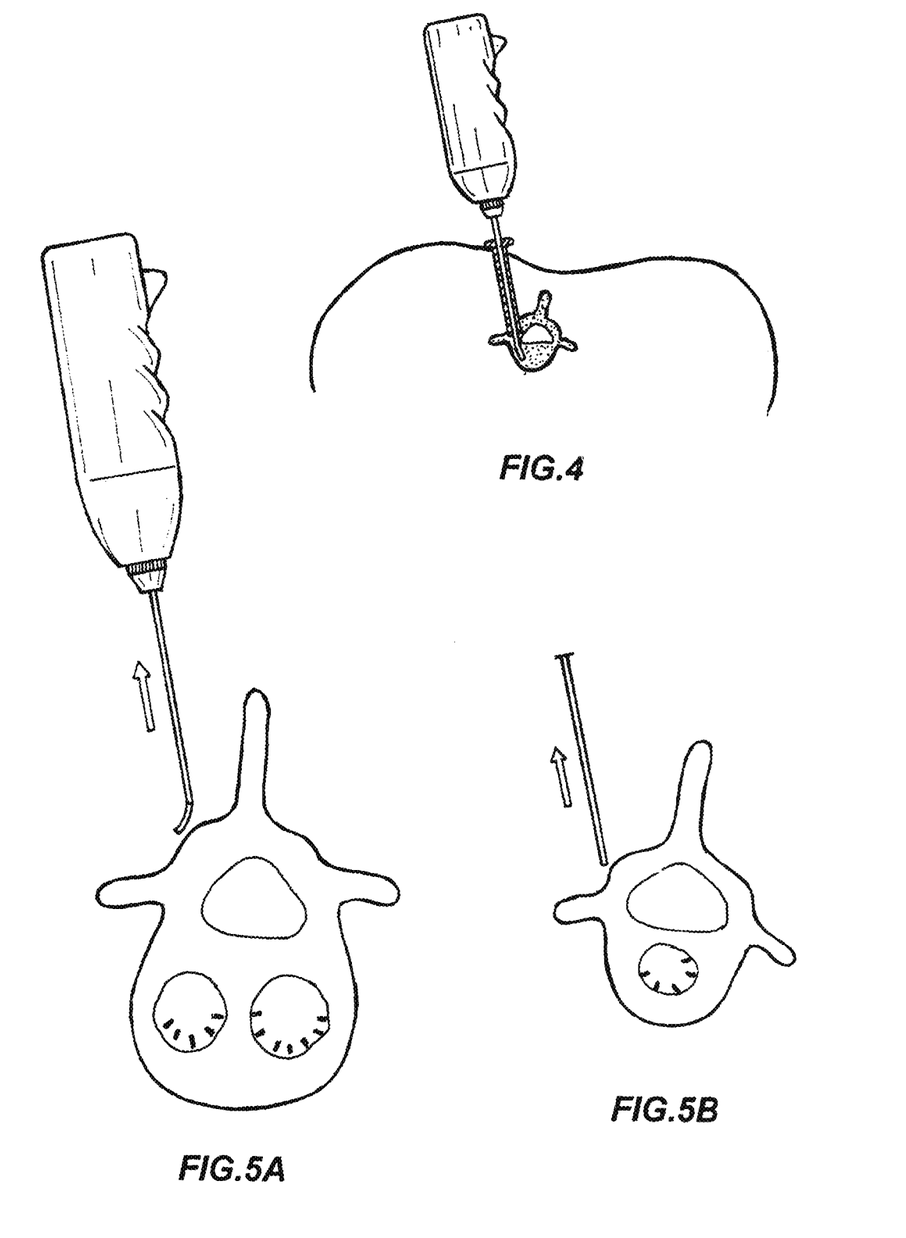
FIG. 4 shows a perspective view of the device of FIG. 1, during an exemplary use for depositing radioactive seeds in a vertebral body.
FIGS. 5A and 5B show each a schematic view of a vertebral body, respectively lumbar with biportal access and dorsal with monoportal access, after insertion of radioactive seeds by the device of FIG. 1.

Referring also to FIG. 3, to the main body 2, and in particular to the distal end thereof, it is removably connected the above-mentioned cannula unit 10, suitable to percutaneous introduction of the radioactive seed in the body site of interest. In particular, the cannula unit 10 is connected or connectible to the main body 2 at a proximal longitudinal end thereof, whereas the opposite, distal, longitudinal end is arranged in the body site, typically within a working cannula 500 per se known. There may be provided means for connecting, and in particular for locking the device 1 and/or the cannula unit 10 to the working cannula 500.

The cannula unit 10 comprises a cannula-holding body 11, preferably of ring nut type, realizing a removable connecting means of the cannula unit 10 itself to the main body 2. In the present example, the cannula-holding body 11 engages a corresponding connecting element 200 for connection of the main body 2. Preferably, such connection is obtained by engagement of respective threads. In a variant embodiment, the connection between main body 2 and cannula unit 10 can be carried out so as to allow a controlled rotation of the latter with respect to the former.

The cannula unit 10 moreover comprises an external cannula 12 and an internal cannula 13, the latter received or receivable within the external cannula 12. The internal cannula 13 has a lumen suitable to enable the sliding of the radioactive seed released from the rotating drum 30 and of the pusher 70 urging it.

The external cannula 12 in turn, comprises a distal tubular element 121 and a proximal bearing element 122, removably connected or connectible the one to the other. In the present example, such parts 121 and 122 are connected by a shape or joint coupling.

The cannula-holding body 11 is removably connected or connectible to the bearing element 122 of the external cannula 12, preferably by a threaded coupling.

The external cannula 12 has, at its own distal end, a distal portion 123 with a profile substantially tilted or curved with respect to the longitudinal direction L. Preferably, such portion 123 defines an angle α of about 30° with respect to the axis L.

The internal cannula 13 has, at its own distal end, a flexible portion 131, suitable to enable the assembling of the cannula unit 10 and a depositing of the radioactive seed according to the tilted direction defined by the tilted-profile distal portion 123. Always at, or in proximity of the distal end, the internal cannula 13 can provide a fall-preventing holding means, e.g. a membrane pierceable by the seed itself when urged by the pusher 70.

Moreover, at the proximal end of the internal cannula 13 an end-of-stroke element 132 for the cannula-holding body 11 may be obtained, typically in the form of an abutment edge.

The assembling of the cannula unit 10, before its connection to the connecting element 200 of the main body 2, can be carried out as follows.

The cannula-holding body 11 is threaded on the internal cannula at the distal end thereof. The bearing element 122 of the external cannula 12 is threaded on the internal cannula 13. Then, on the latter is inserted, from the distal end, the tubular element 121 of the external cannula 12, which is connected to the bearing element 122.

The device 10 may be provided in the form of a kit, comprising also plural cannula units of different length or with different mechanical properties. Moreover, the various cannula units may have a different profile at said distal portion.

The overall arrangement described hereto is such that, in use, the pusher 70 urges the radioactive seed released from the rotating drum 30, overcoming the distal silicone membrane 52 and sliding with its own distal portion within the cannula unit 10. The main direction of sliding, or of advancement, is defined by the longitudinal axis L of the device 1, corresponding to a longitudinal axis of the cannula unit 10. Once the seed has been deposited, it is provided that the pusher be returned into a resting position completely retracted within the pusher-holding element 71.

Advantageously, at the distal end of the pusher 70 a marker, in particular radiopaque, may be provided, for an improved control, before the depositing, of the positioning of the radioactive source.

The device 1 may also be provided as part of an apparatus which also includes a possibly remote control unit, programmable according to different depths of advancement of the pusher 70. Said unit may also receive signals from detecting means such as sensors or transducers, e.g. the above-mentioned encoder. Said unit may be, e.g., a control unit with a display.

Control of the pusher 70, and in general of the various components held in the main body 2, may be obtained with a control system internal to the device 1 or associated to a remote control unit as the one cited above.

The device may be connected or connectible, e.g. by connection cable, with said remote control unit, which may adjust, as said, the progression of the pusher defined for the length of various cannulas and/or depths of advancement.

The remote control unit may bear a battery pack, or anyhow a power-supplying means for the driving of the motor of the device, so as to allow the advancement of the pusher and its retraction. In a different configuration, the same device may bear inside its handpiece the batteries apt to drive the motor, so as to allow the advancement of the pusher and its retraction. In this latter variant, the device may be preset, so as to allow the progression of the pusher to an extent comparable with the length of cannulas of variable length.

The invention also refers to an innovative brachytherapy treatment procedure, which preferably employs the device or the apparatus described hereto.

As said above, such procedure can be utilized for the treatment of primitive and secondary bone tumours, including those from localizations of malignant hemolymphoproliferative diseases, and of malignant tumours of soft tissues.

The procedure may be performed in case of previously operated tumours, incompletely, not concomitantly to the open intervention, or in those in which a recurrence has occurred, and also in multiple lesions, or in small-diameter lone ones, in which an ablative surgical treatment is not indicated, or in cases of patients that, due to general conditions or intrinsic features of the tumour lesion (volumetry, or infiltration of noble structures), cannot be eligible for a surgical treatment.

The procedure could be used also in cases in which an incomplete surgical ablation treatment is to be supplemented with a percutaneous interstitial brachytherapy treatment for the residue, or for other lesions in other sites.

In case of some specific vertebral interventions, the innovative procedure provides that a cavity be obtained in the vertebral body. In such cavity, the seeds could be deposited in a space having a preferably frustoconical shape, to allow an optimum working space to the cannula unit, particularly a rotation of 360° with respect to axis L, with a 30° angle of the terminal of the applying cannula.

Hereinafter, a preferred embodiment of said procedure will be described.

In a first stage, the lesions to be treated may be studied with suitable radiological methods (standard radiographies, Computerized Tomography (CT), Magnetic Resonance, PET-CT, etc.).

Upon singling out an indication to the interstitial brachytherapy procedure, considered herein, said procedure can be carried out under Radioscopy control, and/or in the course of CT examination, preferably in an operating room, or in an Interventional Radiology Room or in a Computerized Tomography Room.

Such method is carried out, as said, percutaneously. It is therefore a method of low surgical risk, with modest or no blood losses; in selected cases, it may also be carried out under local anaesthesia.

In case the lesion be of a small diameter, and therefore there be no indication to a consolidation procedure for the bone segment or the vertebra, a dosimetric study is directly carried out, which will indicate the position of the radioactive sources to be deposited inside the lesion.

For vertebral intrasomatic lesions, in most cases in the dorsal and lumbar sections, under sequential concomitant antero-posterior and latero-lateral radioscopy controls, one or two skin incisions are made (typically of about 10 mm) on the vertical of the articular processes, therefore on the directrix of the peduncles; a monoportal, extrapeduncular approach can be carried out for high dorsal intrasomatic lesions, D3 to D7, obtaining an implantation site central to the vertebral body; for all others, a bilateral approach will be preferred for the creation of two symmetrical sites of implantation.

Said method is carried out in prone position, on a radiotransparent operating bed, in the study and treatment area, preferably under general anaesthesia.

After having positioned the Yamshidi® (produced by Kyphon®/Medtronic®)—which is an instrument apt to penetrate the peduncle to reach a position more anterior with respect to the rear wall of the body—or an equivalent instrument, a Kirschner guide wire is introduced thereinside, in a conventional manner, with the distal end at the middle of the vertebral body, in the place, therefore, of the center of the cavity that will subsequently be created.

On the guide of the Kirschner wires the working cannulas (typically of a 4-mm diameter) are introduced, with the distal end just beyond the rear wall of the vertebra (image checked in latero-lateral under radioscopy). Said wires are preferably graduated, with visible marks every 10 mm, so that by subtracting to the total length of the wire the length of the portion external to the working cannula we may have the exact length of the cannula unit to be connected with the handpiece of the applicator device.

Alternatively, by utilizing a one-step system, the working cannulas are directly introduced in the vertebral body, just beyond the rear wall, removing the piercing mandrel thereof.

Then, collections (by biopsy cannulas or other system) from the vertebral body may be carried out, to the ends of a histopathological study, in order to confirm the nature of the lesion (however already documented with other methods).

In this stage, the Microspeed® arthro system (Aesculap®/B Braun®), or an equivalent system can be introduced inside the working cannulas, for suction of soft parts of the tumour and/or small portions of bone. Terminals of various forms and use may be used, with diameters of from 3.0 to 3.7 mm (already on the market) which can obtain pathological tissue fragmenting and vaporizing.

The cavities are created with the kyphoplasty method already known (adequate inflating of balloons), or with other systems by drill, with cavities of predefined dimensions, or with other methods. In case the cavities do not assume an adequate geometry, a curette may be introduced, steerable at 30°, 60° and 90°, for cruentation of bone trabeculae. Then, the balloons are inflated again.

Cavity(ies) dimensions can be evaluated radioscopically by measuring the expansion of the balloons, filled with radiopaque iodinated contrast medium; the unit of measure of radioscopic images, which may vary in proportion to the position of the radioscopic apparatus emitter with respect to the patient, is obtained by interposing in the image a metal ring which is always the same (or by other similar methods); in operating units availing themselves of intraoperative Computerized Tomography apparatuses, cavity measurements are performed on the images obtained.

The dosimetric study, by the health physic, implies the assessment of dimensions and morphology of the lesions to be treated or of the cavities obtained intraoperatively, establishing, according to a study of isodoses, the type of radioactive sources and the number and position of the same.

Then, one can proceed with the insertion of the radioactive seed(s) with the device of the invention. Said device, and in particular the cannula unit, is fixed to the above-cited known working cannula, previously positioned and stably driven into the vertebral body.

Correct seed positioning can be checked, each time, by antero-posterior and latero-lateral radioscopic images, comparing them with targets singled out by the dosimetric study.

The procedure implies that, notwithstanding the implantation accuracy of the radioactive sources, should one or more of the same be malpositioned with respect to dosimetric indications, owing to bone density features, trabeculae interposition or other causes, even for minimal differences, the source may be removed in the course of the procedure by a known instrument, typically a pincers for endoscopic use.

It will be better appreciated by now that the invention allows a radioactive source positioning extremely safe for the operators, as well as accurate, repeatable and reliable.

Patient's autonomy is immediate, without prescriptions, except radioprotection ones.

Permanent seed implantation will prevent new seed-extracting maneuvers (as in similar brachytherapy procedures).

The invention allows to shorten treatment times with respect to those of a conventional radiotherapy, also because the procedure is carried out in a single session.

The present invention has been hereto described with reference to preferred embodiments thereof. It is understood that other embodiments might exist, all falling within the concept of the same invention, as defined by the protective scope of the claims hereinafter.

The invention claimed is:

1. A portable device for insertion of one or more radioactive seeds in brachytherapy applications, comprising:
   a main body substantially in form of a handpiece;
   a shielded container of the one or more radioactive seeds, received within said main body and having a rotatable drum suitable, in use, to release the one or more radioactive seeds from said container;
   a driver of said rotatable drum, which driver is activatable by an operator;
   an introducer of the one or more radioactive seeds in a body site of interest, comprising a substantially wire-shaped pusher; and
   a synchronizer of the release of the one or more radioactive seeds by said rotatable drum and said introducer;
   wherein, in use, said pusher urges the one or more radioactive seeds released from said rotating drum through a cannula unit, the cannula unit being connected, at a first proximal longitudinal end thereof, to said main body and being percutaneously insertable so that a distal longitudinal end thereof be arranged in the body site.

2. The device according to claim 1, which is suitable to be percutaneously removed immediately after a deposition of the one or more radioactive seeds.

3. The device according to claim 1, wherein said driver of said rotatable drum comprises one or more lever mechanisms.

4. The device according to claim 3, wherein said one or more lever mechanisms are connected to said rotatable drum by a mutual engagement by gears.

5. The device according to claim 1, wherein said driver of said rotatable drum comprises a lever mechanism operable as a trigger actuatable by the operator.

6. The device according to claim 1, wherein said pusher is substantially flexible, so as to be able to follow a guide path within said main body.

7. The device according to claim 1, wherein said introducer further comprises a gears mechanism configured to cause the advancement of said pusher within the cannula unit.

8. The device according to claim 1, wherein said container and/or said rotatable drum are removable, interchangeable and/or rechargeable.

9. The device according to claim 1, wherein said pusher bears, at its own distal end, a marker.

10. The device according to claim 1, comprising said cannula unit, the cannula unit being removably connected or connectible to said main body.

11. The device according to claim 10, wherein said cannula unit comprises an external cannula and an internal cannula, the internal cannula being received or receivable within said external cannula and in turn having a lumen suitable to enable sliding of the one or more radioactive seeds and of said pusher urging them.

12. The device according to claim 11, wherein said external cannula comprises a distal tubular element and a proximal bearing element, removably connected or connectible the one to the other.

13. The device according to claim 12, wherein said cannula unit comprises a removable connector with said main body, which removable connector comprises a cannula-holding body, and wherein said cannula-holding body is removably connected or connectible to said bearing element of said external cannula.

14. The device according to claim 11, wherein said internal cannula has, at its own distal end, a flexible portion.

15. The device according to claim 11, wherein said cannula unit has, at said distal end, a profile substantially tilted or curved with respect to a longitudinal direction of main advancement of the one or more radioactive seeds within the cannula unit.

16. The device according to claim 15, which is provided in the form of a kit comprising one or more cannula units, each having a different profile or tilt at said distal end.

17. The device according to claim 11, which is provided in the form of a kit comprising one or more cannula units.

18. The device according to claim 1, wherein said cannula unit comprises a removable connector with said main body, which removable connector comprises a cannula-holding body.

19. An apparatus for brachytherapy applications, comprising a device according to claim 1 and a control unit programmable according to different depths of advancement of said pusher.

20. The apparatus according to claim 19, comprising a control unit with a display.

21. The apparatus according to claim 19, comprising, in said control unit, a power-supply of said device.

* * * * *